United States Patent
Buechler et al.

(10) Patent No.: US 6,908,739 B2
(45) Date of Patent: Jun. 21, 2005

(54) **DIAGNOSTIC ASSAYS FOR DETECTION OF *GIARDIA LAMBLIA***

(75) Inventors: Joe Buechler, Carlsbad, CA (US); Shanthi Govindaraj, Carlsbad, CA (US); Jeff Gray, Solana Beach, CA (US); Gunars E. Valkirs, Escondido, CA (US)

(73) Assignee: Biosite Incorporated, San Diego, CA (US)

( * ) Notice: Subject to any disclaimer, the term of this patent is extended or adjusted under 35 U.S.C. 154(b) by 39 days.

(21) Appl. No.: 10/155,163

(22) Filed: May 23, 2002

(65) Prior Publication Data

US 2003/0064417 A1 Apr. 3, 2003

Related U.S. Application Data

(62) Division of application No. 09/158,945, filed on Sep. 21, 1998, now abandoned.

(51) Int. Cl.$^7$ ............... G01N 33/53; G01N 33/567; A61K 39/395; A61K 39/02
(52) U.S. Cl. ............... 435/7.1; 424/9.1; 424/130.1; 424/141.1; 424/150.1; 424/164.1; 424/184.1; 424/234.1; 435/4; 435/7.2; 435/7.32
(58) Field of Search .............. 424/9.1, 130.1, 424/141.1, 150.1, 164.1, 184.1, 234.1; 435/4, 7.1, 7.2, 7.32

(56) References Cited

U.S. PATENT DOCUMENTS

| 4,200,690 A | 4/1980 | Root et al. |
| 5,503,983 A | 4/1996 | Rosoff et al. |
| 5,965,375 A | 10/1999 | Valkirs |

FOREIGN PATENT DOCUMENTS

| EP | 0390460 | 10/1990 |
| EP | 0517154 A1 | 12/1992 |

OTHER PUBLICATIONS

Garcia et al., "Detection of *Giardia lamblia*, *Entamoeba histolytical/Entamoeba dispar*, and *Cryptosporidium parvum* Antigens in Human Fecal Specimens Using the Triage Parasite Panel Enzyme Immunoassay," J. of Clinical Microbiology, 38(9) p. 3337–3340.
Harlow, E. and Lane, D., Eds., "Making the Assay Quantitative" *Antibodies: A Laboratory Manual*, Cold Spring Harbor Laboratory (1988) Chapter 14, pp. 553–612.
Alonso et al. (1992) *Mol. Biochem. Parasitol.* 50: 95–104.
Black et al. (1977) *Pediatrics* 60: 486–491.
Crossley et al. (1986) *J. Cell Sci.* 80:233–252.
Green et al. (1985) *Lancet* 2:691–693.
Hassan et al. (1995) *J. Egypt. Soc. Parasitol.* 25:175–182.
Lujan et al. (1995) *J. Biol. Chem.* 270(49): 29307–29313.
Meyer et al. (1980) *Am. J. Epidermiol.* 111(3): 1–12.
Nash et al. 1987) J. Clin. Microbiol. 25: 1169–1171.
Peattie et al. (1989) *J. Cell Biol.* 109: 2323–2335.
Rosoff et al. (1986) *J. Clin. Microbiol.* 24(6): 1079–1083.
Rosoff et al. (1989) *J. Clin. Microbiol.* 27(9): 1997–2002.
Stibbs (1988) *J. Clin. Microbiol.* 26: 1665–1669.
Stibbs (1989) *J. Clin. Microbiol.* 27(11): 2582–2588.
Ungar t al. (1984) *J. Infect. Dis.* 149: 90–97.
Wenman et al. (1993)*Parasitol. Res.* 79: 587–592.

*Primary Examiner*—Rodney P Swartz
(74) *Attorney, Agent, or Firm*—Townsend and Townsend and Crew LLP; Nathan S. Cassell

(57) ABSTRACT

This invention provides methods, reagents, and kits that are useful for diagnosing infection by *Giardia lamblia*. The methods are based on the discovery of binding agents, including recombinant polyclonal antibodies, that bind to the α-1-giardin antigen of *G. lamblia*.

17 Claims, 2 Drawing Sheets

DIAGNOSTIC ASSAYS FOR DETECTION OF GIARDIA LAMBLIA

CROSS-REFERENCE TO RELATED APPLICATIONS

This application is a divisional of, and claims the benefit of priority from, application Ser. No. 09/158,945, filed Sep. 21, 1998, now abandoned, the full disclosures of which are incorporated herein by reference in its entirety and for all purposes.

BACKGROUND OF THE INVENTION

1. Field of the Invention

This invention pertains to the field of diagnostic assays for detecting infection of an animal by the protozoan parasite *Giardia lamblia*.

2. Background

*Giardia* is a protozoan parasite that is a major cause of diarrhea worldwide. The most common species of *Giardia* is *G. lamblia*, which is the most common pathogenic parasite in North America (Meyer and Jarrol (1980) *Am. J. Epidemiol.* 3: 1–12). *Giardia* has two life stages. The trophozoite stage inhabits the small intestine of host animals, moving about using a flagella. A suction disk allows the trophozoite to attach to the wall of the intestine while it feeds on mucous secretions. The second life stage, the cyst, has a stronger outer layer, and thus better able than the trophozoite to survive outside of the host while passing from host to host. Transmission is typically through *Giardia*-contaminated water supplies (Meyer and Jarrol, supra.), or person to person (Black et al. (1977) *Pediatrics* 60: 486–491).

The cytoskeleton of *G. lamblia* trophozoites contain a group of 29–38 kDa proteins known as giardins (Peattie et al. (1989) *J. Cell Biol.* 109: 2323–2335). Nucleic acid sequences are known for several of the giardins, including α-1-giardin and α-2-giardin, which are 81% identical at the nucleic acid level and have amino acid sequences that are 77% identical (Alonso and Peattie (1992) *Mol. Biochem. Parasitol.* 50: 95–104). The α-1-giardin has been identified on the membrane and disk of *G. lamblia* trophozoites (Wenman et al. (1993) *Parasitol. Res.* 79: 587–592).

Traditionally, *Giardia* infection is diagnosed by microscopic detection of ova and parasites (O&P) in stools, which is a laborious process. More recently developed methods for *Giardia* diagnosis include serologic tests for anti-*Giardia* antibodies. Little correlation was found, however, between the presence of anti-*Giardia* antibodies in the serum and active *Giardia* infection. Other diagnostic methods involve detection of *Giardia* antigens in stool samples. For example, Green et al. discuss the use of an affinity-purified antiserum raised by inoculating rabbits with whole trophozoites or disrupted trophozoites and cysts (Green et al. (1985) *Lancet* 2: 691–693). Other groups have described the use of mono-specific antibodies that bind to a 65 kDa antigen that is shed in the stool of giardiasis patients (Rosoff and Stibbs (1986) *J. Clin. Microbiol.* 24: 1079–1083; U.S. Pat. No. 5,503,983; Stibbs (1989) *J. Clin. Microbiol.* 27: 2582–2588; Rosoff et al. (1989) *J. Clin. Microbiol.* 27: 1997–2002). Monoclonal antibodies that bind to two species of *Giardia* cyst wall constituents are discussed in Lujan et al. (1995) *J. Biol. Chem.* 270: 29307–29313. ELISA assays for *G. lamblia* are discussed in, for example, Nash et al. (1987) *J. Clin. Microbiol.* 25: 1169–1171; Stibbs et al. (1988) *J. Clin. Microbiol.* 26: 1665–1669; Ungar et al. (1984) *J. Infect. Dis.* 149: 90–97.

Previously described assays for detecting *Giardia* infection often have shortcomings. For example, the assay of Ungar et al. was reported to fail to detect 8% of positive samples, and cannot be read by direct visual inspection (Green et al., supra.). Therefore, a need exists for improved methods for detecting *Giardia* infection in animals, including humans. The present invention fulfills this and other needs.

SUMMARY OF THE INVENTION

The present invention provides methods of diagnosing infection of a mammal by a *Giardia* species, in particular *G. lamblia*. The methods involve contacting a capture reagent which binds to an α-1-giardin of *G. lamblia* with a stool sample obtained from the mammal. The capture reagent forms a complex with the α-1-giardin if the α-1-giardin is present in the test sample. The presence or absence of the α-giardin bound to the capture reagent is then detected; the presence of the α-1-giardin is indicative of *Giardia* infection of the mammal.

The invention also provides devices and kits for diagnosing infection of a mammal by a *Giardia* species, in particular *G. lamblia*. The kits typically include, inter alia, a solid support upon which is immobilized a capture reagent which binds to an α-1-giardin of *G. lamblia*, and a detection reagent which binds to the α-1-giardin.

Also provided by the invention are recombinant monoclonal and polyclonal antibodies that bind to α-1-giardin.

BRIEF DESCRIPTION OF THE DRAWINGS

FIG. 1A is a top view, showing an elongated well in the center. FIG. 1B is a section view of the top piece, showing a membrane that is ultrasonically welded to the underside of the top piece. FIG. 1C is an end view of the top piece of the apparatus.

FIG. 2A is a top view, FIG. 2B is a section view, and FIG. 2C is an end view of the bottom piece. To construct a complete apparatus, a bottom piece is joined to a top piece such as is shown in FIGS. 1A–1C.

DETAILED DESCRIPTION

Definitions

Figure 1C:
FIGS. 1A–1C show a top piece of an apparatus for performing an immunoassay for detecting *G. lamblia* infection in a sample.

The phrases "specifically binds to" or "specifically immunoreactive with", when referring to an antibody or other binding moiety refers to a binding reaction which is determinative of the presence of a target antigen in the presence of a heterogeneous population of proteins and other biologics. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity. Typically a specific or selective reaction will be at least twice background signal or noise and more typically more than 10 to 100 times background. Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The term "epitope" means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (See, e.g., Paul, *Fundamental Immunology*, 3$^{rd}$ Ed., 1993, Raven Press, New York).

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al. (1987) *J. Mol. Biol.* 196: 901–917; (1989) *Nature* 342: 878–883; and (1989) *J. Mol. Biol.* 186: 651–663.

The term "antibody" is used to mean whole antibodies and binding fragments thereof. Binding fragments include single chain fragments, Fv fragments and Fab fragments The term Fab fragment is sometimes used in the art to mean the binding fragment resulting from papain cleavage of an intact antibody. The terms Fab' and F(ab')$_2$ are sometimes used in the art to refer to binding fragments of intact antibodies generated by pepsin cleavage. Here, "Fab" is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the CH1 domain of the constant region.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

Description of the Preferred Embodiments

The invention provides methods, reagents, and kits that are useful for diagnosing infection of a mammal by a *Giardia* species, in particular *G. lamblia*. The assays provide a rapid, accurate and cost-effective means for detecting *Giardia* infection. The methods of the invention are both sensitive and specific, and can be used for detecting a *Giardia* antigen that is soluble.

The methods, compositions and kits provided by the instant invention are useful for detecting *Giardia* infection in test samples, including biological samples such as cultures, tissue samples, bodily fluids, and the like. Typically, the biological sample analyzed for *Giardia* infection will be a stool sample. For liquid or semi-solid stool samples, a portion of the sample is added to an assay container and, optionally, diluted with a suitable diluent such as water or an appropriate buffer and mixed. Suitable buffers include, for example, buffered protein solutions and the like. Solid stool samples can be placed in a diluent and suspended by vigorous mixing. Typically, the sample is diluted sufficiently to provide a solution of suitable clarity for use in the assays; this is generally about a 3–20 fold dilution, with about a 10-fold dilution being typical. After mixing, one can clarify the sample by, for example, filtration or centrifugation or other methods known to those of skill in the art. In general, well known methods for preparing test samples for assays, such as immunoassays, are suitable for preparing test samples for analysis using the methods provided by the invention.

A. Assay Reagents

The assays of the invention involve detecting the presence in a biological sample of an α-giardin, in particular α-1-giardin, which is an antigen that is specific for *Giardia*. The α-1-giardin nucleotide and predicted amino acid sequences have been reported (Alonso and Peattie, supra.; Wenman et al., supra.); GenBank Accession No. U94701).

The invention provides assay reagents that are capable of specifically binding to α-giardins, including the α-1-giardin antigen. These assay reagents can be used in one or more steps of the assay. For example, the assay reagents can be immobilized on a solid support and used to immobilize the giardin on a solid support. Assay reagents can also be used to detect the *Giardia* antigens by, for example, attaching a detectable label to a binding moiety that binds to the α-giardin. These are discussed in greater detail below.

The assay means for detecting the giardin are, in some embodiments, binding assays. In these assays, which include immunoassays, the giardin is detected using detection reagents that are capable of specifically binding to α-1-giardin. The detection reagents include at least a binding moiety and a detectable label. Suitable binding moieties include any molecule that is capable of specifically binding to α-1-giardin. Antibodies and fragments thereof are examples of binding components that are suitable for use in detection moieties.

Various procedures known in the art can be used for the production of antibodies that specifically bind to α-1-giardin. For the production of polyclonal antibodies, one can use α-1-giardin to inoculate any of various host animals, including but not limited to rabbits, mice, rats, sheep, goats, and the like. The α-1-giardin can be prepared by recombinant means using an expression vector containing a gene encoding the antigen; the complete nucleotide sequence is available in GenBank, Accession No. U94701.

Monoclonal antibodies can be prepared by any technique that provides for the production of antibody molecules by continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO8912690, published Dec. 12, 1989) and U.S. Pat. No. 5,091,512.

Fragments of antibodies are also useful as binding moieties. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275–1281; these techniques facilitate rapid identification of monoclonal Fab fragments with the desired specificity for α-1-giardin. Suitable binding moieties also include those that are obtained using methods such as phage display.

To prepare a suitable antigen preparation, one can prepare a cDNA expression library from *G. lamblia* and screen the library with a polyclonal antibody that is raised against a crude preparation of α-1-giardin. The cDNA inserts from those expression plasmids that express the α-1-giardin are then subcloned and sequenced. The α-1-giardin-encoding inserts are cloned into an expression vector and used to transform *E. coli* or other suitable host cells. The resulting preparation of recombinant α-1-giardin is then used to inoculate an animal, e.g., a mouse.

In preferred embodiments, the assay reagents use recombinantly produced polyclonal or monoclonal antibodies that bind to the α-1-giardin as binding moieties. Recombinant antibodies are typically produced by immunizing an animal with the α-giardin, obtaining RNA from the spleen or other antibody-expressing tissue of the animal, making cDNA, amplifying the variable domains of the heavy and light immunoglobulin chains, cloning the amplified DNA into a phage display vector, infecting *E. coli*, expressing the phage display library, and selecting those library members that express an antibody that binds to α-giardin. Methods suitable for carrying out each of these steps are described in, for example U.S. patent application Ser. No. 08/835,159, filed Apr. 4, 1997. In preferred embodiments, the antibody or other binding peptides are expressed on the cell surface of a replicable genetic unit, such as a filamentous phage, and especially phage M13, Fd and F1. Most work has inserted libraries encoding polypeptides to be displayed into either gIII or gVIII of these phage, forming a fusion protein which is displayed on the surface of the phage. See, e.g., Dower, WO 91/19818; Devlin, WO 91/18989; MacCafferty, WO 92/01047 (gene III); Huse, WO 92/06204; Kang, WO 92/18619 (gene VIII).

In a preferred embodiment, the genes that encode the heavy and light chains of antibodies present in the cDNA library are amplified using a set of primers that can amplify substantially all of the different heavy and light chains. The resulting amplified fragments that result from the amplification step are pooled and subjected to asymmetric PCR so that only one strand (e.g., the antisense strand) is amplified. The single strand products are phosphorylated, annealed to a single-stranded uracil template (e.g., the vector BS45, described in U.S. patent application Ser. No. 08/835,159, which has coding regions for the constant regions of mouse heavy and light chains), and introduced into a uracil DNA glycosylase$^+$ host cell to enrich for vectors that contain the coding sequences for heavy and light chain variable domains.

To screen for phage that express an antibody that binds to α-1-giardin, one can attach a label to α-1-giardin using methods known to those of skill in the art. In a preferred embodiment, the phage that display such antibodies are selected using α-1-giardin to which is attached an immobilizable tag, e.g., biotin. The phage are contacted with the biotinylated antigen, after which the phage are selected by contacting the resulting complex with avidin attached to a magnetic latex bead or other solid support. The selected phage are then plated, and may be screened with α-1-giardin to which is attached a detectable label.

In a preferred embodiment, the library is enriched for those phage that display more than one antibody that binds to α-1-giardin. Methods and vectors that are useful for this enrichment are described in U.S. patent application Ser. No. 08/835,159. The panning can be repeated one or more times to enhance the specificity and sensitivity of the resulting antibodies. Preferably, panning is continued until the percentage of functional positives is at least about 70%, more preferably at least about 80%, and most preferably at least about 90%.

A recombinant anti-1-giardin monoclonal antibody can then be selected by amplifying antibody-encoding DNA from individual plaques, cloning the amplified DNA into an expression vector, and expressing the antibody in a suitable host cell (e.g., *E. coli*). The antibodies are then tested for ability to bind α-1-giardin. An example of a recombinant monoclonal antibody prepared using this method is the mAb GL.5; cells that produce this antibody were deposited under the Budapest Treaty with the American Type Culture Collection (10801 University Boulevard, Manassas, Va. 20110-2209) on Sep. 1, 1998, and the deposit has been assigned ATCC Accession No. 98858.

Recombinant polyclonal antibodies are particularly preferred, in particular because of the various forms of α-1-giardin that may be found in clinical samples due to, for example, proteolysis. The diverse fine binding specificity of members of a population of polyclonal antibodies often allows the population to bind to several forms of α-1-giardin (e.g., species variants, escape mutant forms) to which a monoclonal reagent may be unable to bind. Methods for producing recombinant polyclonal antibodies are described in co-pending, commonly assigned U.S. patent application Ser. No. 08/835,159, filed Apr. 4, 1997. Specific methods of producing recombinant polyclonal antibodies that bind to α-1-giardin are described in the Examples below.

Polyclonal antibodies can be prepared as described above, except that an individual antibody is not selected. Rather, the pool of phage are used for the screening, preferably using an equal number of phage from each sample. In preferred embodiments, the phage are enriched for those that display more than one copy of the respective antibodies. The phage are then selected for those that bind to α-1-giardin. For example, one can use a biotinylated anti-1-giardin monoclonal antibody and α-1-giardin to concentrate those phage that express antibodies that bind to α-1-giardin. The biotinylated monoclonal antibody is immobilized on a solid support (e.g., magnetic latex) to which is attached avidin. The phage that are bound to the immobilized α-1-giardin are eluted, plated, and the panning repeated until the desired percentage of functional positives is obtained.

B. Assay Formats

The assays for detecting *Giardia* infection can be performed in any of several formats. For example, a sandwich assay can be performed by preparing a biological sample as discussed above, or as is otherwise appropriate for the particular sample, and placing the sample in contact with a solid support on which is immobilized a plurality of capture reagents that bind α-1-giardin. The α-1-giardin, if present in the sample, binds to the capture reagents. The solid support is then contacted with detection reagents for α-1-giardin. The solid support can be washed prior to contact with detection reagents to remove unbound reagents. After incubation of the detection reagents for a sufficient time to bind a substantial portion of the immobilized α-1-giardin, any unbound labeled reagents are removed by, for example, washing. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the specific antigen in the sample.

The capture reagent can be any compound that specifically binds to α-1-giardin. Examples of binding moieties that are suitable for use as capture reagents are described above. One example of a suitable capture reagent is the recombinant polyclonal antibody preparation GL.18.PC, which was prepared as described in the Examples. Cells that produce these recombinant polyclonal antibodies were deposited under the Budapest Treaty with the American Type Culture Collection (10801 University Boulevard, Manassas, Va. 20110-2209) on Sep. 1, 1998, and have been assigned-ATCC Accession No. 98853.

To immobilize α-1-giardin on the solid support, a capture reagent that specifically binds to α-1-giardin is non-diffusively associated with the support. The capture reagents can be non-diffusively immobilized on the support either by covalent or non-covalent methods, which are known to those of skill in the art. See, e.g., Pluskal et al. (1986) *BioTechniques* 4: 272–283. Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, and also particles, such as agarose, SEPHADEX™, and the like. Assay systems for use in the methods and kits of the invention include, but are not limited to, dipstick-type devices, immunochromatographic test strips and radial partition immunoassay devices, and flow-through devices. Conveniently, where the solid support is a membrane, the sample will flow through the membrane, for example, by gravity, capillary action, or under positive or negative pressure.

Preferred assay systems for use in the kits and methods of the invention are described in EP 447154. These systems employ an apparatus that includes a porous member such as a membrane or a filter onto which is bound a multiplicity of anchor moieties for α-1-giardin. The apparatus also includes a non-absorbent member with a textured surface in communication with the lower surface of the porous member. The textured surface of the non-absorbent member can be a grooved surface such as the surface of a record or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid. In some embodiments, the capillary communication between the porous member and the non-absorbent member favors delaying the transferal of fluid from the porous member to the capillary network formed by the porous member and the textured surface of the non-absorbent member until the volume of the added fluid substantially exceeds the void volume of the porous member. The transferal of fluid from the porous member to the network of capillary channels formed by the porous member and the textured surface of the non-absorbent member can occur without the use of external means, such as positive external pressure or vacuum, or contact with an absorbent material. The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the sample is added to the porous member, where the sample permeates the void volume of the porous member and thereby contacts the anchor moieties immobilized on the porous member. In a non-competitive assay, the sample to be assayed is applied to the porous member and the α-1-giardin, if present, is bound by the anchor moieties. A detection reagent for α-1-giardin is then added as an additional fluid; these bind to the complex of α-1-giardin and capture reagent. Alternatively, the detection reagent can be added to the sample prior to application of the sample to the porous member so that the binding of detection reagent to α-1-giardin occurs prior to the binding of α-1-giardin to the capture reagent. In another embodiment, the capture reagent and detection reagent are added to the sample, after which the complex of capture reagent, α-1-giardin, and detection reagent binds to a binding agent that is either combined with these reagents or is immobilized on the porous member. An additional fluid containing reagents to effect a separation of free from bound labeled reagents can be added to remove excess detection reagent, if needed.

This device is designed to provide sufficient sensitivity to measure low concentrations of α-1-giardin because one can use large amounts of sample and efficiently remove the excess of detection reagent. Indeed, the efficient separation of free from bound label achieved by the network of capillary channels of this device improves the discrimination of specific α-1-giardin-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor. This method enables the detection of α-1-giardin in a manner that is simple, rapid, convenient, sensitive and efficient in the use of reagents.

Competitive binding assays can also be used to detect α-1-giardin. Conveniently, these assays are performed using the described devices by adding to a sample a labeled analog of α-1-giardin. The labeled analog and α-1-giardin present in the sample compete for the binding sites of the capture reagents. Alternatively, the capture reagents can be combined with the sample and labeled analogs with subsequent immobilization of the capture reagents onto the porous member through contact with a binding agent. An additional fluid to separate the free from bound label may be added to the device, followed if needed by a signal development solution to enable detection of the label of the labeled analog which has complexed with capture reagent immobilized on the porous member. The amount of labeled α-1-giardin bound to the porous member is related to the concentration of α-1-giardin in the sample.

This invention also provides kits for the detection and/or quantification of α-1-giardin by the described methods. The kits can include a container containing one or more of the above-discussed detection reagents with or without labels, and capture reagents, either free or bound to solid supports. Also included in the kits can be a suitable membrane, preferably in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. An internal control can consist of α-1-giardin. The control antigen can conveniently be preattached to a capture reagent in a zone of the solid support adjacent to the zone to which the sample is applied. The external control can also consist of α-1-giardin. Typically, the antigen present in the external control will be at a concentration at or above the sensitivity limit of the assay means. The external control antigen can be diluted in the sample diluent and assayed in the same manner as would a biological sample. Alternatively, the external control α-1-giardin can be added to an aliquot of an actual biological sample to determine the sensitivity of the assay. The kits of the present invention can contain materials sufficient for one assay, or can contain sufficient materials for multiple assays.

The methods, compositions and kits provided by the invention are capable of detecting α-1-giardin with high sensitivity. The assays and kits will detect α-1-giardin when present in a sample at a concentration of about 100 ng/ml or less. Preferably, the detection limit for α-1-giardin will be about 20 ng/ml or less, more preferably about 4 ng/ml or less, and still more preferably the detection limit for α-1-giardin will be about 1 ng/ml or less.

C. Detection Reagents

The presence of α-1-giardin is generally detected using a detection reagent that is composed of a binding moiety that specifically binds to α-1-giardin. The detection reagents are either directly labeled, i.e., comprise or react to produce a detectable label, or are indirectly labeled, i.e., bind to a molecule comprising or reacting to produce a detectable label. Labels can be directly attached to or incorporated into the detection reagent by chemical or recombinant methods.

In one embodiment, a label is coupled to a molecule, such as an antibody that specifically binds to α-1-giardin, through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue Published by Molecular Probes, Inc., Eugene, Oreg. Patents that described the use of such labels include U.S. Pat. Nos. 3,817,837; 3,850,752; 3,939, 350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention in the clinic, preferred labels are non-radioactive and readily detected without the necessity of sophisticated instrumentation. Preferably, detection of the labels will yield a visible signal that is immediately discernable upon visual inspection. One preferred example of detectable secondary labeling strategies uses an antibody that recognizes $\alpha$-1-giardin in which the antibody is linked to an enzyme (typically by recombinant or covalent chemical bonding). The antibody is detected when the enzyme reacts with its substrate, producing a detectable product. Preferred enzymes that can be conjugated to detection reagents of the invention include, e.g., $\beta$-galactosidase, luciferase, horse radish peroxidase, and alkaline phosphatase. The chemiluminescent substrate for luciferase is luciferin. One embodiment of a fluorescent substrate for $\beta$-galactosidase is 4-methylumbelliferyl-$\beta$-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3, 2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

EXAMPLES

The following examples are offered to illustrate, but not to limit the present invention.

Example 1

Generation and Screening of *Giardia lamblia* cDNA Libraries

This Example describes the cloning of cDNAs that encode the $\alpha$-1-giardin antigen of *Giardia lamblia*.

A. Preparation of Soluble Antigen from *Giardia lamblia*

*Giardia lamblia* WB strain, ATCC 30957, was cultured in Diamond's TYI-S-33 medium (Diamond et al. (1978) *Trans. R. Soc. Trop. Med. Hyg.* 72: 431–432) supplemented with 10% heat-inactivated calf serum (Sigma, St. Louis, Mo.). The encystation of *Giardia lamblia* was performed as described (Gillin et al. (1988) *Infect. Immun.* 56: 705–707). Organisms were harvested and washed three times in 0.01M phosphate buffered saline (PBS), pH 7.6. The cell pellet was resuspended in 1 ml of PBS and subjected to 4 cycles of flash-freezing and thawing. *Giardia lamblia* trophozites and cysts were sonicated for 4 min using a VirSonic 475 Ultrasonic Cell Disrupter. Cell disruption was monitored by microscopic inspection. Cells and debris were removed by centrifugation at 14,000×g for 20 min at 4° C. The supernatant containing soluble antigen was transferred to a fresh tube, assayed for protein content, and used for immunizations.

B. Isolation and Purification of RNA from *Giardia lamblia* Trophozoite, 5 hr Cyst, and 24 hr Cyst Cultures.

Approximately $10^8$ organisms from three separate cultures representing different phases of the *Giardia lamblia* encystation process (trophozoite, 5 hr cyst, and 24 hr cyst) were washed in ice-cold, sterile PBS (phosphate buffered saline) and subjected to centrifugation in an IEC tabletop centrifuge at 3,500 rpm for 30 min at 4° C. Working quickly, 1.0 ml of solution D (25.0 g guanidine thiocyanate (Boehringer Mannheim, Indianapolis, Ind.), 29.3 ml sterile water, 1.76 ml 0.75M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)) was added to the pellet while vortexing. The cell suspension was pulled through an 18-gauge needle until viscous and all cells were lysed, then transferred to a microcentrifuge tube. The suspension was then pulled through a 22-gauge needle an additional 5–10 times.

The sample was divided evenly between two microcentrifuge tubes and the following added in order, with mixing by inversion after each addition: 100 μl 2M sodium acetate (pH 4.0), 1.0 ml water saturated phenol (Fisher Scientific, Pittsburgh, Pa.), 200 μl chloroform/isoamyl alcohol 49:1 (Fisher Scientific, Pittsburgh, Pa.). The solution was vortexed for 10 seconds and incubated on ice for 15 minutes. Following centrifugation (10,000 g) for 20 minutes at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 minutes at 2–8° C., and the aqueous phase was transferred to a fresh tube and precipitated with an equal volume of isopropanol at −20° C. for a minimum of 30 minutes. Following centrifugation (10,000 g) for 20 minutes at 4° C., the supernatant was aspirated away, the tubes briefly spun and all traces of liquid removed.

The RNA pellets were each dissolved in 300 µl of solution D, combined, and precipitated with an equal volume of isopropanol at −20° C. for a minimum of 30 minutes. The sample was centrifuged (10,000 g) for 20 minutes at 4° C., the supernatant aspirated as before, and the sample rinsed with 100 µl of ice-cold 70% ethanol. The sample was again centrifuged (10,000 g) for 20 minutes at 4° C., the 70% ethanol solution aspirated, and the RNA pellet dried in vacuo. The pellet was resuspended in 100 µl of sterile distilled water. The concentration was determined by $A_{260}$ using an absorbance of 1.0 for a concentration of 33 µg/ml. The RNAs were stored at −80° C.

Messenger RNA (mRNA) was purified from total RNA using Oligotex Mini-Kit mRNA isolation kit (Qiagen, Santa Clarita, Calif.) according to manufacturer's recommendations. The concentration was determined by $A_{260}$ using an absorbance of 1.0 for a concentration of 40 µg/ml. The mRNAs were stored at −80° C.

C. Synthesis of Lambda cDNA Libraries.

The mRNAs (5.0 µg) purified above were used to synthesize the first and second strands of cDNA using a cDNA synthesis kit (Stratagene, San Diego, Calif.) following the manufacturer's recommendations. The resulting cDNAs were selected for inserts greater than 500 base pairs in length. The size-selected cDNAs were then ligated into the Uni-ZAP XR vector (Stratagene, San Diego, Calif.) and packaged with Gigapak™ Gold packaging extract (Stratagene, San Diego, Calif.) following the manufacturer's recommendations. The primary sizes for the trophozoite, 5 hr cyst, and 24 hr cyst libraries were determined by plating serial dilutions of the packaged library (see below) to be $8.7 \times 10^6$, $1.5 \times 10^7$, and $6.5 \times 10^6$ plaque-forming units (pfu), respectively. Background was determined to be approximately 2% through blue/white selection (see below). The resulting Uni-ZAP XR lambda phage library was amplified once before screening to ensure stability of the library, titered, and stored at 4° C.

D. Plating Lambda Phage cDNA Library.

Starting with a lambda phage stock, a series of 100-fold dilutions (10 µl to 1.0 ml) were made in SM buffer (Stratagene, San Diego, Calif.). The diluted phage samples (10 µl) were added to 200 µl of an overnight culture of Escherichia coli strain XL1-Blue MRF' (Stratagene, San Diego, Calif.) adjusted to $OD_{600}=0.5$ in 10 mM $MgSO_4$ in sterile 15 ml tubes and incubated at 37° C. for 15 min. After adding 3.0 ml of NZY top-agar at 55° C., the mixture was poured and evenly distributed on an NZY agar plate (100 mm) that had been pre-warmed (37° C.–55° C.) to remove any excess moisture on the agar surface. The plates were cooled to room temperature, at which time the top-agar solidified, and the plates were inverted and placed at 37° C.

For titering purposes, the plates were left at 37° C. overnight and the number of plaques counted and a titer determined. In order to determine the background for the library (the percentage of clones not carrying an insert), several hundred plaques were plated as described above. Prior to plating, 15 µl of 0.5M isopropyl-β-D-thiogalactoside (IPTG) and 50 µl of 5-bromo-4-chloro-3-indoyl-β-d-galctopyranoside (X-gal) [250 mg/ml (in dimethylformamide)] was added to the NZY top agar. These plates were incubated at 37° C. for 6–8 hours and transferred to room temperature overnight. Plaques that stained blue correspond to clones that do not have an insert, while non-staining, white plaques contain an insert. The percentage of background plaques was calculated by dividing the number of blue plaques by the total number of plaques.

E. Screening of G. lamblia Trophozoite, 5 hr Cyst, and 24 hr Cyst cDNA Libraries with Monoclonal Antibody GL.5

The G. lamblia trophozoite, 5 hr cyst, and 24 hr cyst cDNA libraries were plated, separately, on large (150 mm) NZY agar plates at a density of approximately 10,000–20,000 pfu/plate as described above, except that 600 µl of $OD_{600}=0.5$ XL1-Blue cells and nine ml of NZY top agar were used for plating. When the plaques reached 0.5–1.0 mm in diameter (4–5 hr), nitrocellulose filter lifts (diameter 137 mm, pore size 0.45 µm, BA85 Protran, Schleicher and Schuell, Keene, N.H.) soaked in 10 mM isopropyl-β-D-thiogalactoside (IPTG) were placed on the agar plates, marked asymmetrically with a needle, and placed at 20° C.

After overnight incubation, the filters were carefully removed from the plates with membrane forceps, rinsed briefly in TBST (40 mM TRIS, 150 mM NaCl, 0.05% Tween 20 (Fisher Chemical, Pittsburgh, Pa.), pH 7.5) to remove any debris from the lifts, and incubated for greater than 1 hr in block (1% BSA solution containing 20 mM Tris, 150 mM NaCl, and 0.1% sodium azide, pH 8.0). The filters were then incubated in GL.5-alkaline phosphatase (AP) conjugate (prepared as described in Example 19A) at 2.5 µg/ml, in block, for a minimum of four hours. The filters were washed three times with TBST for five min each.

After the final wash, the filters were developed as described in Example 14. The filters were aligned with the agar plates through the asymmetric needle marks and plaques individually cored from the agar plates and transferred to 250–500 µl of SM buffer. The plaques were chosen based on their staining intensity with GL.5-AP conjugate, ranging from light staining to dark staining. These plaques were purified to homogeneity through iterative rounds of the plating/filter lift procedure described above.

The DNA inserts were subcloned into the plasmid vector pBluescript™ (Stratagene, San Diego, Calif.) through an in vivo excision process following manufacturer's recommendations. The DNA sequence at the 3' end of each clone was determined by the dideoxy chain termination method using Sequenase™ II DNA cloning kit (U.S. Biochemical) and an oligonucleotide, primer A (Table 1), that binds to the DNA sequence on the 3' side of the insert in the pBluescript vector. A total of five clones were sequenced of which four, representing all three libraries, produced readable sequence that was identical in all four clones. A search of the sequence against the National Center for Biotechnology Information (NCBI) non-redundant nucleotide database using the BLAST search engine revealed the clones to be Giardia lamblia α-1-giardin (Peattie et al. (1989) J. Cell Biol. 109: 2323–2325).

TABLE 1

PCR and Sequencing Primer Sequences

| | | |
|---|---|---|
| A: | 5'-GTAAAACGACGGCCAGTGAATTG-3' | (SEQ ID NO:1) |
| B: | 5'-ACCCGTTTTTTTGGATGGAGTGAAACGATGCCGAAGGTCACCGACAT TG-3' | (SEQ ID NO:2) |

TABLE 1-continued

PCR and Sequencing Primer Sequences

| | | |
|---|---|---|
| C: | 5'-GTGATAAACTACCGCATTAAAGCTTATCGATGATAAGCTGTCAATTA GTGATGGTGATGGTGATGCTTCACGCGCCAGAGGGTGC-3' | (SEQ ID NO:3) |
| D | 5'-GCGACGGTCTCGTGCCAGTC-3' | (SEQ ID NO:4) |
| E | 5'-CTCCGCACTCGGGACGGTGC-3' | (SEQ ID NO:5) |
| F | 5'-TCGTCGCCCTTGTCATTGCAG-3' | (SEQ ID NO:6) |
| G | 5'-GCAACTCTCTACTGTTTCTCC-3' | (SEQ ID NO:7) |
| H | 5'-GAGGATGACGATGAGCGC-3' | (SEQ ID NO:8) |
| I | 5'-TCGCTGCCCAACCAGCCATG-3' | (SEQ ID NO:9) |
| J | 5'-GTGATAAACTACCGCATTAAAGCTTATCGATGATAAGCTGTCAATTAGT GATGGTGATGGTGATGACAATCCCTG-3' | (SEQ ID NO:10) |

Example 2

Cloning of the *Giardia lamblia* α-1-giardin Antigen cDNA

PCR primers were made corresponding to the 5'-end of the coding sequence of the *G. lamblia* α-1-giardin antigen and the 3'-end of the coding (primers B and C, respectively, Table 1). The 3' oligonucleotide also had six histidine codons inserted between the end of the coding sequence and the stop codon to assist in purification of the recombinant protein by metal-chelate chromatography. In addition, the 5' primer contains 20 base pairs of vector sequence at its 5'-end corresponding to the 3'-end of the pBRnsiH3 vector (described in copending, commonly assigned U.S. patent application Ser. No. 08/835,159, filed Apr. 4, 1997). The 3' primer contains the 19 base pairs of the tet promoter removed by HindIII digestion, in addition to 20 base pairs of vector sequence 3' to the HindIII site at its 5' end (see, Example 18 of U.S. patent application Ser. No. 08/835,159).

The α-1-giardin insert was amplified using the primers described above and one ml of a *G. lamblia* trophozoite lysate as template per reaction. The DNA insert was amplified (3×100 μl reactions) with Expand™ DNA polymerase and the reactions were pooled and purified as described in Example 19 of U.S. patent application Ser. No. 08/835,159. The α-1-giardin insert (150 ng) was annealed with pBRnsiH3 (250 ng) at a 3:1 molar excess of insert to vector, and an aliquot electroporated into 40 μl of electrocompetent *E. coli* strain DH10B as described in Example 10. The transformed cells were diluted to 1.0 ml with 2×YT broth and 10 μl, 100 μl, 300 μl plated on LB agar plates supplemented with tetracycline (10 μg/ml) and grown overnight at 37° C. Colonies were picked into 3 ml 2×YT supplemented tetracycline (10 μg/ml) and grown overnight at 37° C. The following day, glycerol freezer stocks were made for long term storage at −80° C.

The sequence of these clones was verified by the dideoxy chain termination method using Sequenase™ II DNA cloning kit (U.S. Biochemical) and oligonucleotide, primers D–F (Table 1), that bind to the α-1-giardin DNA sequence and primers G and H (Table 1) that bind on the 5' and 3' side of the insert in the pBR vector, respectively. The α-1-giardin antigen was expressed and purified as described in Example 3. The α-1-giardin antigen was biotinylated as described in Example 11.

Example 3

Expression and Purification of Recombinant Antibodies and α-1-giardin Antigen

This Example describes the expression of α-1-giardin, or recombinant antibodies that bind to α-1-giardin, using recombinant *E. coli* cells that contain genes encoding the α-1-giardin antigen of *Giardia lamblia* or antibodies against this antigen.

A. Expression and Purification of Recombinant Antibodies

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) *Bio/Technology* 11: 1271–1277) supplemented with 3 g/L L-leucine, 3 g/L L-isoleucine, 12 g/L casein digest (Difco, Detroit, Mich.), 12.5 g/L glycerol and 10 μg/ml tetracycline. The temperature, pH and dissolved oxygen in the fermentor were controlled at 26° C., 6.0–6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17000 psi. The high pressure homogenization of the cells releases the Fab into the culture supernatant.

The first step in purification was expanded bed immobilized metal affinity chromatography (EB-IMAC). Streamline Chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% NaN$_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% NaN$_3$, pH 8.0. The Fab elution pool from the EB-IMAC step was diluted four-fold in 20 mM borate, 0.01% NaN$_3$, pH 8.0 and loaded onto the IEC column. After washing, the Fab was eluted with a 37.5–200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% NaN$_3$, pH 8.0 buffer for storage. This was achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/ml solution.

B. Expression and Purification of α-1-giardin

A shake flask inoculum was generated overnight from a −70° C. cell bank in an incubator shaker set at 37° C., 300 rpm. The cells were cultured in a defined medium described above. The inoculum was used to seed a 2 L Tunair shake flask (Shelton Scientific, Shelton, Conn.) which was grown at 37° C., 300 rpm. Expression was induced by addition of L(+)-arabinose to 2 g/L during the logarithmic growth phase, following which, the flask was maintained at 23° C., 300 rpm. Following batch termination, the culture was passed through an M-110Y Microfluidizer (Microfluidics, Newton, Mass.) at 17000 psi. The homogenate was clarified in a J2-21 centrifuge (Beckman, Fullerton, Calif.).

Purification employed immobilized metal affinity chromatography. Chelating Sepharose FastFlow resin (Pharmacia, Piscataway, N.J.) was charged with 0.1 M NiCl$_2$ and equilibrated in 20 mM borate, 150 mM NaCl, 10 mM imidazole, 0.01% NaN$_3$, pH 8.0 buffer. A stock solution was used to bring the culture supernatant to 10 mM imidazole and 2-mercaptoethanol was added to 1 mM. The culture supernatant was then mixed with the resin and incubated in the incubator shaker set at room temperature, 150–200 rpm. The antigen was captured by means of the high affinity interaction between nickel and the hexahistidine tag on the antigen. The culture supernatant and resin mixture is poured into a chromatography column. After washing, the antigen was eluted with 20 mM borate, 150 mM NaCl, 200 mM imidazole, 1 mM 2-mercaptoethanol, 0.01% NaN$_3$, pH 8.0 buffer. The antigen pool was concentrated in a stirred cell fitted with a 10,000 MWCO membrane (Amicon, Beverly, Mass.). It was then dialyzed overnight into 20 mM borate, 150 mM NaCl, 0.01% NaN$_3$, pH 8.0 for storage, using 12–14,000 MWCO dialysis tubing. The purified antigen was evaluated for purity by SDS-PAGE analysis. The concentration of the α-1-giardin was measured by UV absorbance at 280 nm, assuming an absorbance of 1.22 for a one mg/ml solution.

Example 4

Immunization of Mice with Crude *Giardia* Soluble Antigen and Purification of RNA from Mouse Spleens Mice were immunized by the following method based on experience of the timing of spleen harvest for optimal recovery of mRNA coding for antibody. Two species of mice were used: Balb/c (Charles River Laboratories, Wilmington, Mass.) and A/J (Jackson Laboratories, Bar Harbor, Me.). Mice were immunized intraperitoneally or subcutaneously with *Giardia* soluble antigen (Example 1A) using 50 µg protein in Freund's complete adjuvant on day 0, and with 100 µg antigen on day 28. Tests bleeds of mice were obtained through puncture of the retro-orbital sinus. If, by testing the titers, they were deemed high by ELISA using biotinylated antigen immobilized via streptavidin, the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 µl of solution D to recover any remaining spleen, and this was transferred to the tube. The suspension was then pulled through a 22 gauge needle an additional 5–10 times.

The sample was divided evenly between two microcentrifuge tubes and the following added, in order, with mixing by inversion after each addition: 100 µl 2 M sodium acetate (pH 4.0), 1.0 ml water-saturated phenol (Fisher Scientific, Pittsburgh, Pa.), 200 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile distilled water. The concentration was determined by $A_{260}$ using an absorbance of 1.0 for a concentration of 40 µg/ml. The RNA was stored at −80° C.

Example 5

Preparation of Complementary DNA (cDNA)

The total RNA purified as described above was used directly as template for cDNA. RNA (50 µg) was diluted to 100 μL with sterile water, and 10 μL of 130 ng/μL oligo dT$_{12}$ (synthesized on Applied Biosystems Model 392 DNA synthesizer) was added. The sample was heated for 10 min at 70° C., then cooled on ice. Forty μL 5× first strand buffer was added (Gibco/BRL, Gaithersburg, Md.), along with 20 μL 0.1 M dithiothreitol (Gibco/BRL, Gaithersburg, Md.), 10 μL 20 mM deoxynucleoside triphosphates (dNTP's, Boehringer Mannheim, Indianapolis, Ind.), and 10 μL water on ice. The sample was then incubated at 37° C. for 2 min. Ten μL reverse transcriptase (Superscript™ II, Gibco/BRL, Gaithersburg, Md.) was added and incubation was continued at 37° C. for 1 hr. The cDNA products were used directly for polymerase chain reaction (PCR).

Example 6

Amplification of cDNA by PCR

To amplify substantially all of the H and L chain genes using PCR, primers were chosen that corresponded to substantially all published sequences. Because the nucleotide sequences of the amino terminals of H and L contain considerable diversity, 33 oligonucleotides were synthesized to serve as 5' primers for the H chains, and 29 oligonucleotides were synthesized to serve as 5' primers for the kappa L chains as described in co-pending, commonly assigned U.S. patent application Ser. No. 08/835,159, filed Apr. 4, 1997. The constant region nucleotide sequences required only one 3' primer each to the H chains and the kappa L chains. Id.

Amplification by PCR was performed separately for each pair of 5' and 3' primers. A 50 μL reaction was performed for each primer pair with 50 pmol of 5' primer, 50 pmol of 3' primer, 0.25 μL Taq DNA Polymerase (5 units/μL, Boehringer Mannheim, Indianapolis, Ind.), 3 μL cDNA (prepared as described in Example 5), 5 μL 2 mM dNTP's, 5 μL 10×Taq DNA polymerase buffer with MgCl$_2$ (Boehringer Mannheim, Indianapolis, Ind.), and H$_2$O to 50 μL. Amplification was done using a GeneAmp® 9600 thermal cycler (Perkin Elmer, Foster City, Calif.) with the following program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only a 3' primer to generate substantially only the anti-sense strand of the target genes. A 100 μL reaction was done for each dsDNA product with 200 pmol of 3' primer, 2 μL of ds-DNA product, 0.5 μL Taq DNA Polymerase, 10 μL 2 mM dNTP's, 10 μL 10×Taq DNA polymerase buffer with MgCl$_2$ (Boehringer Mannheim, Indianapolis, Ind.), and H$_2$O to 100 μL. The same PCR program as that described above was used to amplify the single-stranded (ss)-DNA.

Example 7

Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2–8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 μL water and the L chain products were pooled separately in 210 μL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 2, and the oven temperature was at 60° C. Absorbance was monitored at 260 nm. The ss-DNA eluted from the HPLC was collected in 0.5 min fractions. Fractions containing ss-DNA were ethanol precipitated, pelleted and dried as described above. The dried DNA pellets were pooled in 200 μL sterile water.

TABLE 2

| HPLC gradient for purification of ss-DNA | | | | |
|---|---|---|---|---|
| Time (min) | % A | % B | % C | Flow (ml/min) |
| 0 | 70 | 30 | 0 | 0.75 |
| 2 | 40 | 60 | 0 | 0.75 |
| 32 | 15 | 85 | 0 | 0.75 |
| 35 | 0 | 100 | 0 | 0.75 |
| 40 | 0 | 100 | 0 | 0.75 |
| 41 | 0 | 0 | 100 | 0.75 |
| 45 | 0 | 0 | 100 | 0.75 |
| 46 | 0 | 100 | 0 | 0.75 |
| 51 | 0 | 100 | 0 | 0.75 |
| 52 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The ss-DNA was phosphorylated on the 5' end in preparation for mutagenesis (Example 9). Twenty-four μL 10× kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio) :chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/ml for an absorbance of 1.0. Samples were stored at −20° C.

Example 8

Preparation of Uracil Templates Used in Generation of Spleen Antibody Phage Libraries One ml of *E. coli* CJ236 (BioRAD, Hercules, Calif.) overnight culture was added to 50 ml 2×YT in a 250 ml baffled shake flask. The culture was grown at 37° C. to OD$_{600}$=0.6, inoculated with 10 μl of a 1/100 dilution of BS45 vector phage stock (described in co-pending, commonly assigned U.S. patent application Ser. No. 08/835,159, filed Apr. 4, 1997) and growth continued for 6 hr. Approximately 40 ml of the culture was centrifuged at 12 krpm for 15 minutes at 4° C. The supernatant (30 ml) was transferred to a fresh centrifuge tube and incubated at room temperature for 15 minutes after the addition of 15 μl of 10 mg/ml RNaseA (Boehringer Mannheim, Indianapolis, Ind.). The phage were precipitated by the addition of 7.5 ml of 20% polyethylene glycol 8000 (Fisher Scientific, Pittsburgh, Pa.)/ 3.5M ammonium acetate (Sigma Chemical Co., St. Louis, Mo.) and incubation on ice for 30 min. The sample was centrifuged at 12 krpm for 15 min at 2–8° C. The supernatant was carefully discarded, and the tube was briefly spun to remove all traces of supernatant. The pellet was resuspended in 400 µl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and ⅕ volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 µl sterile water and the concentration determined by $A_{260}$ using an absorbance of 1.0 for a concentration of 40 µg/ml. The template was diluted to 250 ng/µl with sterile water, aliquoted, and stored at −20° C.

Example 9

Mutagenesis of Uracil Template with ss-DNA and Electroporation Into *E. coli* to Generate Antibody Phage Libraries Antibody phage display libraries were generated by simultaneously introducing single-stranded heavy and light chain genes onto a phage display vector uracil template. A typical mutagenesis was performed on a 2 µg scale by mixing the following in a 0.2 ml PCR reaction tube: 8 µl of (250 ng/µl) uracil template (Example 8), 8 µl of 10× annealing buffer (200 mM Tris pH 7.0, 20 mM MgCl₂, 500 mM NaCl), 3.33 µl of kinased single-stranded heavy chain insert (100 ng/µl), 3.1 µl of kinased single-stranded light chain insert (100 ng/µl), and sterile water to 80 µl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 µl of 10× synthesis buffer (5 mM each dNTP, 10 mM ATP, 100 mM Tris pH 7.4, 50 mM MgCl₂, 20 mM DTT), 8 µl T4 DNA ligase (1 U/µl, Boehringer Mannheim, Indianapolis, Ind.), 8 µl diluted T7 DNA polymerase (1 U/µl, New England BioLabs, Beverly, Mass.) and incubating at 37° C. for 30 min. The reaction was stopped with 300 µl of mutagenesis stop buffer (10 mM Tris pH 8.0, 10 mM EDTA).

The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µl of sterile water.

One µl mutagenesis DNA (500 ng) was transferred into 40 µl electrocompetent *E. coli* DH12S (Gibco/BRL, Gaithersburg, Md.) using the electroporation conditions in Example 10. The transformed cells were mixed with 1.0 ml 2×YT broth (Sambrook et al., supra) and transferred to 15 ml sterile culture tubes. The first round antibody phage was made by shaking the cultures overnight at 23° C. and 300 rpm. The efficiency of the electroporation was measured by plating 10 µl of $10^{-3}$ and $10^{-4}$ dilutions of the cultures on LB agar plates (see Example 13). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$. The overnight cultures from the electroporations were transferred to 1.5 ml tubes, and the cells were pelleted by centrifuging at 14 krpm for 5 min. The supernatant, which is the first round of antibody phage, was then transferred to 15 ml sterile centrifuge tubes with plug seal caps.

Example 10

Transformation of *E. coli* by Electroporation

The electrocompetent *E. coli* cells were thawed on ice. DNA was mixed with 20–40 µL electrocompetent cells by gently pipetting the cells up and down 2–3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately diluted to 1 ml with 2×YT broth and processed as procedures dictate.

Example 11

Preparation of Biotinylated Antigens and Biotinylated Antibodies

*Giardia* trophozoite soluble antigen (7.7 mg/ml) and *Giardia* 24 hour cyst soluble antigen (2.1 mg/ml) were reduced by adding DTT to a final concentration of 1 mM. After incubating the antigen at room temperature for 30 min, each antigen was passed through a Sephadex G-50 desalting column (Amersham Pharmacia Biotech, Piscataway, N.J.) equilibrated in column buffer (50 mM potassium phosphate, 10 mM borate, 150 mM NaCl, 0.1 mM EDTA, pH 7.0). Each antigen preparation was split into fractions. One fraction was reacted with biotin-XX-NHS ester (Molecular Probes, Eugene, Oreg., stock solution at 80 mM in dimethylformamide) at a final concentration of 1.0 mM for the cyst antigen and 0.5 mM for the trophozoite antigen. A second fraction was reacted with 3-(N-maleimidylpropionyl) biocytin (Molecular Probes, Eugene, Oreg., stock solution at 50 mM in BBS, pH 8) at a final concentration of 1.0 mM for each antigen preparation. Reaction tubes were incubated at room temperature for 90 min. After 90 min, each mixture was dialyzed extensively against BBS at 2–8° C. After dialysis, the antigen concentrations were estimated to be 50% of the starting material. Each biotinylated antigen preparation was diluted to $10^{-6}$ M, assuming that the average molecular weight of the antigens is 50,000 mg/mmol. Antigen biotin samples were stored at −80° C.

Alpha-1-giardin was extensively dialyzed into BBS. Antigen (1 mg/ml, 1 ml) was reacted with biotin-XX-NHS ester (0.5 mM, 40 mM stock solution in DMF) for 90 min at room temperature. After 90 min, the antigen was dialyzed extensively into BBS and stored at −80° C. Antibodies were reacted with 3-(N-maleimidylpropionyl)biocytin using the free cysteine at the carboxy terminus of the heavy chain. The cysteine was reduced by adding DTT to a final concentration of 1 mM for 30 min at room temperature. The antibody was passed through a Sephadex G50 desalting column equilibrated in column buffer. 3-(N-maleimidylpropionyl)biocytin was added to a final concentration of 1 mM. Reactions were allowed to proceed at room temperature for 60 minutes. Antibodies were dialyzed extensively into BBS and stored at 2–8° C.

Example 12

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet. While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/ml BSA, 0.1% Tween 20 (Fisher Scientific, Pittsburgh, Pa.), pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 13

Plating M13 Phage or Cells Transformed with Antibody Phage-Display Vector Mutagenesis Reaction The phage samples were added to 200 µL of an overnight culture of E. coli XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C., Appendix A1, Sambrook et al., supra.), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Example 14

Developing Nitrocellulose Filters with Alkaline Phosphatase Conjugates

After overnight incubation of nitrocellulose filters on the LB agar plates, the filters were carefully removed from the plates with membrane forceps and incubated for 2 hr in block. After 2 hr, the filters were incubated with goat anti-mouse kappa-AP (Southern Biotechnology Associates, Inc, Birmingham, Ala.) for 2–4 hr. The goat anti-mouse kappa-AP conjugate was diluted into block at a final concentration of 1 µg/ml. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/ml nitro blue tetrazolium (Fisher Scientific, Pittsburgh, Pa.) and 0.166 mg/ml 5-bromo-4-chloro-3-indolyl-phosphate, p-toluidine salt.

Example 15

Selection of Polyclonal Antibodies to Crude Soluble α-1-giardin Antigen

The first round antibody phage was prepared as described in Example 9 using BS45 uracil template. Electroporations of mutagenesis DNA were performed yielding phage samples derived from different immunized mice. To create more diversity in the polyclonal library, each phage sample was panned separately. The antibody phage (about 0.9 ml) from each electroporation was transferred to a 15 ml disposable sterile centrifuge tube with a plug seal cap. BSA (30 µL of 300 mg/ml solution) and 1 M Tris (50 µL, 1 M stock solution, pH 8.0) were added to each phage stock. Five µl of $10^{-6}$ M *Giardia* trophozoite soluble antigen-biotin (maleimide reaction of Example 11) and 5 µl of $10^{-6}$ M *Giardia* trophozoite soluble antigen-biotin (NHS ester reaction of Example 11) were added to phage samples derived from the spleens of mice immunized with *Giardia* trophozoite soluble antigen. The same amounts of *Giardia* soluble cyst antigen-biotin (maleimide reaction of Example 11 and NHS ester reaction of Example 11) were added to phage samples derived from the spleens of mice immunized with *Giardia* soluble cyst antigen. The antibody phage were allowed to come to equilibrium with the antigen-biotin by incubating the phage at 2–8° C. overnight.

After the incubation, the phage samples were panned with avidin magnetic latex. The equilibrated avidin magnetic latex (see Example 12), 200 µL latex per sample, was incubated with the phage for 10 min at room temperature. After 10 min, approximately 9 ml of panning buffer was added to each phage sample, and the magnetic latex was separated from the solution using a magnet. After a ten minute separation, the unbound phage was carefully removed using a 10 ml sterile pipette. The magnetic latex was then resuspended in 10 ml of panning buffer to begin the second wash. The latex was washed a total of four times as described above. For each wash, the tubes were in contact with the magnet for 10 min to separate unbound phage from the magnetic latex. After the fourth wash, the magnetic latex was resuspended in 1 ml of panning buffer and transferred to a 1.5 ml tube.

The entire volume of magnetic latex for each sample was then resuspended in 200 µL 2YT and was plated on 150 mm LB plates as described in Example 13. The 150 mm plates were used to amplify the phage binding to the magnetic latex to generate the next round of antibody phage. These plates were incubated at 37° C. for 4 hr, then overnight at 20° C. After the overnight incubation, the second round antibody phage was eluted from the 150 mm plates by pipetting 10 ml 2YT media onto the lawn and gently shaking the plate at room temperature for 20 min. The phage samples were transferred to 15 ml disposable sterile centrifuge tubes with plug seal cap, and the debris from the LB plate was pelleted by centrifuging the tubes for 15 min at 3500 rpm. The second round antibody phage was then transferred to a new tube.

The second round of panning was set up by diluting 100 µL of each phage stock into 900 µL panning buffer in 15 ml disposable sterile centrifuge tubes with plug seal cap. The biotinylated *Giardia* antigen was added to each sample as described for the first round of panning, and the phage samples were incubated overnight at 2–8° C. The phage samples were panned with avidin magnetic latex following the overnight incubation as described above. After washing the latexes with panning buffer, each latex was plated on 150 mm LB agar plates. The plates were incubated at 37° C. for 4 hr, then overnight at 20° C. The third round antibody phage was eluted as described above.

Panning phage samples as described above or enriching the phage samples prior to functional panning (see Example 16 of U.S. patent application Ser. No. 08/835,159, 7F11 magnetic latex) was continued until the percentage of kappa positives in the phage was greater than 60%. Individual phage samples from the trophozoite antigen panning were pooled and the phage samples from panning with cyst antigen were separately pooled. The pooled trophozoite phage and the pooled cyst phage were subcloned into the expression vector, pBRncoH3. The subcloning was done generally as described in U.S. patent application Ser. No. 08/835,159, Example 18.

Example 16

Analysis of Polyclonal Antibodies to Crude *Giardia* Antigen and Selection of Monoclonal Antibodies The polyclonal antibodies from the trophozoite library and the polyclonal antibodies from the cyst library were conjugated to alkaline phosphatase and biotinylated. The sensitivity of each polyclonal antibody was determined by performing a sandwich assay using the same polyclonal antibody (biotinylated for capture and conjugated to AP for detection) on both sides of the sandwich. Assays can be performed with streptavidin coated plates such as Reacti-Bind Streptavidin coated polystyrene 96 well plates (Pierce Chemical, Rockford, Ill.).

After washing the 96 well plate with a plate washer like the Skan Washer (Skatron Instruments, Sterling, Va.), biotinylated polyclonal antibody (50 µL of 2.5 µg/ml diluted in block) was added to 12 wells. The plate was incubated at room temperature for 1 hr. The plate was washed, then 96 hr *Giardia* cysts (50 µl) were added in duplicate to the biotinylated polyclonal wells at three different concentrations, 26,000 cysts/ml, 5200 cysts/ml, and 1040 cysts/ml. Trophozoites were added in duplicate to the remaining wells at three different concentrations, 38,500 trophozoites/ml, 7700 trophozoites/ml, and 1540 trophozoites/ml. Antigen was incubated for 1 hr at room temperature, then the plate was washed. The polyclonal antibody alkaline phosphatase conjugate (50 µl of 2.5 µg/ml diluted in block) was added and incubated at room temperature for 1 hr.

After 1 hr, the plate was washed and developed using the ELISA Amplification System (Gibco BRL, Gaithersburg, Md.) according to the manufacturer's instructions. The trophozoite polyclonal antibody gave a signal above background for both 96 hr cysts and trophozoites at all three dilutions of antigen. This verified that sensitive antibodies were present in the polyclonal antibody preparation. It was desired to have a monoclonal/polyclonal antibody pair to one specific antigen. The trophozoite polyclonal frozen stock was streaked out onto LB agar plates supplemented with tetracycline (10 µg/ml). Individual colonies were picked off the plate into 2YT media and tetracycline (10 µg/ml) and grown overnight at 37° C., 300 rpm. These monoclonal antibodies were expressed and purified as described in Example 3.

Each antibody was used to develop a Western blot of soluble *Giardia* antigen. Antibodies that gave a strong signal to an antigen were further characterized. Monoclonal antibody GL.5 recognized a band at approximately 30 kDa. This monoclonal was used to probe the *Giardia* cDNA libraries to identify the antigen.

Example 17

Selection and Cloning of Polyclonal Antibody Complementary to GL.5

Phage libraries were made using cDNA from the spleens of animals that had been immunized with *Giardia* trophozoites and cysts, and the phage were panned as described in Example 15 using biotinylated α-1-giardin instead of the crude soluble antigen. The first three rounds of panning were done using biotinylated α-1-giardin at $10^{-8}$M. The fourth round antibody phage was panned with 7F11 magnetic latex prior to the functional panning with biotinylated α-1-giardin at $10^{-8}$ M.

After the fourth round of panning with biotinylated α-1-giardin, individual antibody phage samples were pooled using an equal volume of phage from each sample. Biotinylated monoclonal antibody (GL.5, 12 µl, $10^{-6}$M) and α-1-giardin (12 µl $5 \times 10^{-8}$M) were mixed and incubated for 10 min at room temperature. Twenty µl of antibody biotin/antigen was added to the phage sample, and the sample was incubated overnight at 2–8° C. The sample was panned with avidin magnetic latex and plated as described in Example 15. The eluted phage was panned a second time as described with the mixture of biotinylated GL.5 and α-1-giardin. The phage eluted after the second round of panning were subcloned as described in Example 18 of U.S. patent application Ser. No. 08/835,159. This polyclonal was designated GL.18.PC.

Example 18

Microtiter Plate Assay Sensitivity

The sensitivity of the monoclonal/polyclonal antibody pair was determined by performing a sandwich assay using biotinylated GL.5 and alkaline phosphatase conjugated GL.18.PC (prepared as described in Example 19A). After washing the 96 well plate with a plate washer (see Example 11), biotinylated GL.5 (50 µl of 2.5 µg/ml diluted in block) was added to 12 wells. The plate was incubated at room temperature for one hour. The plate was washed, then purified α-1-giardin (50 µl) was added in duplicate to the biotinylated monoclonal wells at five different concentrations of antigen, 20 ng/ml, 10 ng/ml, 5 ng/ml, 2.5 ng/ml and 1.25 ng/ml, and block was added to the last two wells for the blank. Antigen was incubated for 1 hr at room temperature, then the plate was washed. The complementary polyclonal alkaline phosphatase conjugate (GL.18.PC, 50 µl of 2.5 µg/ml diluted in block) was added and incubated at room temperature for 1 hr. After 1 hr, the plate was washed and developed using the ELISA Amplification System according to the manufacturer's instructions. The signal was read at 490 nm using a microplate reader (Molecular Devices, Sunnyvale, Calif.). Table 3 shows the signal at 490 nm versus the concentration of giardin antigen.

TABLE 3 concentration of α-1-giardin antigen versus signal at 490 nm (endpoint reading) for the antibody pair GL.5/GL.18.PC

| Concentration (ng/mL) | Absorbance (490 nm) |
| --- | --- |
| 0 | 0.108 |
| 1.25 | 0.382 |
| 2.5 | 0.637 |
| 5 | 1.191 |
| 10 | 1.933 |
| 20 | 2.752 |

Example 19

Preparation and Testing of Device for Detecting *Giardia lamblia* Infection

This Example describes the preparation and testing of a device for detecting *Giardia lamblia* infection. The device employs the recombinant polyclonal antibody to immobilize α-1-giardin on a solid support, and a recombinant monoclonal antibody to detect the presence of immobilized α-1-giardin.

A. Preparation of Antibody-Alkaline Phosphatase Conjugates for Use as Detection Reagents.

Detection reagents for use in the assay were prepared by conjugating alkaline phosphatase to antibodies for the α-1-giardin antigen. The recombinant monoclonal antibody GL.5 was used to detect α-1-giardin. Alkaline phosphatase (AP, Calzyme Laboratories, San Luis Obispo, Calif.) was dialyzed against a minimum of 100 volumes of column buffer (50 mM potassium phosphate, 10 mM borate, 150 mM NaCl, 1 mM $MgSO_4$, pH 7.0) at 2–8° C. for a minimum of four hours and the buffer was changed at least twice prior to use of the AP. After the AP was removed from dialysis and brought to room temperature, the concentration was determined by determining the $A_{280}$, with an absorbance of 0.77 indicating a 1 mg/ml solution. The AP was diluted to 5 mg/ml with column buffer.

For crosslinking the AP to the antibody, AP was first linked to succinimidyl 4-(N-maleimidomethyl cyclohexane-1-carboxylate (SMCC, Pierce Chemical Co., Rockford Ill.) using a 20:1 ratio of SMCC:AP. SMCC was dissolved in acetonitrile at 20 mg/ml and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G-50 Fine, Pharmacia Biotech, Piscataway, N.J.) in a column equilibrated with column buffer.

Recombinant antibodies were reacted with 1 mM dithiothreitol (DTT, Calbiochem, San Diego, Calif.) for 30 minutes at room temperature to reduce a cysteine residue present near the carboxy terminus of the heavy chain constant region. The DTT was separated from the antibody by gel filtration chromatography using G50 Fine in column buffer without $MgSO_4$ but containing 0.1 mM ethylenediaminetetraacetic acid (EDTA, Fisher Scientific, Pittsburgh, Pa.). The AP and the antibody were mixed together in a molar ratio of six antibodies to one alkaline phosphatase and the conjugation reaction was allowed to continue for one hour at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using SEPHACRYL™ S-200 HR (Pharmacia Biotech, Piscataway, N.J.). The free antibody was excluded from the conjugate pool which was diluted for use in immunoassays in a conjugate diluent containing 1% bovine serum albumin (from 30% BSA, Bayer, Kankakee. Ill.), 2% casein (Hammersten grade, Research Organics, Cleveland, Ohio), 100 mM trehalose (Aldrich Chemical Co., Milwaukee, Wis.), 50 mM potassium phosphate, 150 mM sodium chloride, 1 mM $MgSO_4$, 0.1 mM $ZnCl_2$, 0.1% polyvinyl alcohol (80% hydrolyzed, Aldrich Chemical Co., Milwaukee Wis.), pH 7.0.

B. Preparation of Antibody-Casein Conjugates for Use as Capture Reagents

Capture reagents for the α-1-giardin antigen were prepared as follows. Where recombinant antibodies were used as capture reagents, the antibodies were first conjugated to casein. Casein was dissolved in deionized water at 2.5% solids by stirring it at 37–45° C. while adding concentrated potassium hydroxide to keep the pH of the solution between 7 and 8. After the pH had stabilized at 7.0, the casein was diluted with deionized water to a final $A_{280}$ of 10. The casein solution was subjected to tangential flow filtration through an ultrafiltration membrane with a molecular weight cut-off of 300,000 in order to exclude aggregated protein from the filtrate. The casein filtrate was concentrated to a final $A_{280}$ of approximately 10 by ultrafiltration. A solution of SMCC was prepared at 20 mg/ml (60 mM) in acetonitrile; this was diluted into the casein solution to a final concentration of 2 mM SMCC. The solution was allowed to stand for 90 minutes at room temperature and then was subjected to gel filtration chromatography in a column containing G50 Fine equilibrated in column buffer in order to separate the protein from the reactants. The casein was mixed with recombinant antibody GL.18.PC that had been reacted with 1 mM DTT and subjected to gel filtration chromatography to remove the DTT as described in Example 19A above. The antibody was mixed with the casein in a 4:1 molar ratio and the reaction was allowed to proceed for one hour at room temperature before the conjugation was stopped as described above. The conjugate solution was subjected to gel filtration chromatography in a column containing SEPHACRYL™ S-200 HR in order to separate the conjugated antibody from the unconjugated antibody. The conjugated antibody was concentrated using an ultrafiltration membrane and subjected to dialysis vs. borate-buffered saline (BBS, 20 mM borate, 150 mM sodium chloride, 0.02% sodium azide, pH 8.2) and stored in BBS until immobilization on nylon membranes.

C. Preparation of Assay Devices

The assays were performed using capture reagents that were immobilized on nylon membranes. Recombinant Fab antibodies were conjugated to casein as described above prior to immobilization. The antibodies were immobilized on the nylon membranes (5 μm pore size; IMMUNODYNE™, Pall Corporation, Glen Cove, N.Y.) in a continuous process by pumping an antibody solution directly onto the membrane while the membrane was moved past a stationary nozzle which dispensed the antibody solution at a flow rate controlled by the pump. The antibody solution typically contained antibody at a concentration between 1 and 5 mg/ml in a buffer containing 20 mM borate, 150 mM sodium chloride, 0.02% sodium azide, and 10% trehalose, pH 8.2.

Each antibody was immobilized in a line approximately 0.040 inches wide, such that approximately 36 μL of antibody solution was required per linear foot of membrane. The antibody solution applied to the membrane was dried prior to blocking the entire membrane by saturating it with a solution containing 2% casein, 40% STABILICOAT™ (Bio-metric Systems, Eden Prairie, Minn.), 0.25% TRITON X-100™ (Sigma Chemical Co., St. Louis, Mo.) and drying the membrane in a drying tunnel or in a dry room. The antibody can also be applied in spots by applying a volume of approximately 1 µL of antibody solution to the membrane at the desired location prior to blocking and drying the membrane. Generally, several lines of immobilized antibody were placed on a membrane in this manner and the membrane was cut perpendicular to the direction of the antibody lines for placement in the assay devices.

Figure 1A:
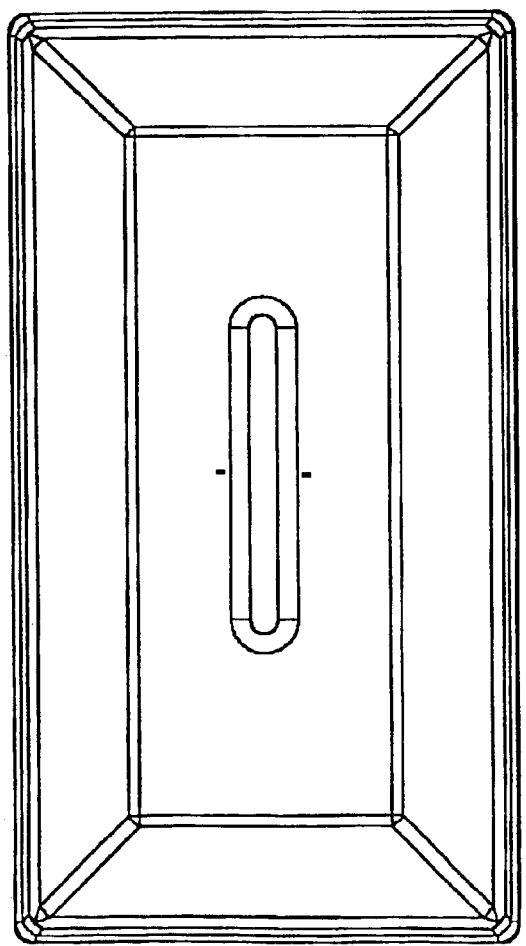
Figure 1B:
Figure 2C:
FIGS. 2A–2C show a bottom piece of an apparatus for performing an immunoassay for detecting *G. lamblia* infection in a sample.
Figure 2A:
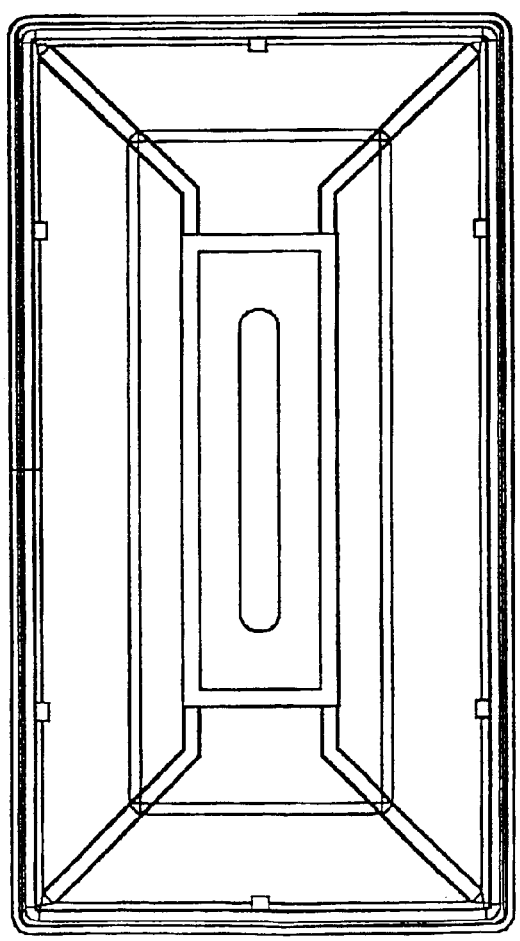
Figure 2B:

The cut membrane pieces were ultrasonically welded to an opening in a plastic device top (see FIG. 1A—top view, FIG. 1B—side section, and FIG. 1C—end view) which was then ultrasonically welded to a plastic bottom piece (see FIG. 2A—top view, FIG. 2B—side section, and FIG. 2C—end view) having grooves cut into its upper surface. The contact between the membrane and the two plastic pieces resulted in a network of capillary channels that caused fluids added to the membrane to flow through the membrane and into the capillary network between the two plastic pieces. Such devices are described in European Patent Application No. 447154.

For the immunoassay of α-1-giardin, a total of three lines of antibody were immobilized on the membrane. The top line in the device was a positive control for the immunoassay of α-1-giardin. The antibody solution used in the immobilization step for the positive control contained α-1-giardin at approximately 1 µg/ml mixed with the GL.18.PC-casein conjugate at approximately 1 mg/ml. The next line on the membrane was for the capture and detection of α-1-giardin. The solution used to immobilize the antibody for α-1-giardin contained approximately 2 mg/ml of the GL.18.PC antibody conjugated to casein. The last line of immobilized antibody on the device was a negative control line; the antibody solution used to apply this line to the membrane contained a recombinant polyclonal antibody (2 mg/ml) that was specific for an antigen not found in *Giardia lamblia*.

For filtering samples prior to performing the assays, disposable filter devices were constructed using standard 10-cc plastic syringes. Disks of filter material were cut to a diameter that would allow the disk to be placed into the barrel of the syringe so that sufficient contact was created between the syringe barrel and the edge of the filter disk. This prevented fluids from bypassing the filter material when liquid samples were forced through the filter by the plunger. At the bottom of the syringe closest to the outlet was a disk of glass fiber filter (GF/F, 0.7 µm, Whatman, Clifton, N.J.) followed by a disk of porous plastic (Porex Technologies, Fairbum, Ga.). The next two disks of filter material were both cut from CELLUPORE™ filter grade 850 material (Cellulo Co., Fresno, Calif.). The next disk of filter material was cut from CELLUPORE™ filter grade 315 material (Cellulo Co., Fresno, Calif.). The uppermost filter element in the syringe barrel was a bonded cellulose acetate material (American Filtrona, Richmond, Va.) that served as a prefilter for the filter elements described previously. An alternative filter device that contains essentially the same elements is the AUTOVIAL™ (Whatman, Clifton, N.J.) which is a disposable syringe that has a GMF glass fiber filter with a rating of 0.45 µm already connected to the end of the syringe. The other filter elements described above were placed in the barrel of the AUTOVIAL™ in the same order.

D. Immunoassay of α-1-giardin

Stool samples (approximately 0.5 g or 0.5 ml) were diluted tenfold with sample diluent containing 1% casein, 100 mM potassium phosphate, 150 mM sodium choride, 0.1% Dow 193 surfactant (Dow Coming, Midland, Mich.), 0.1% bovine IgG (Sigma Chemical Co., St. Louis, Mo.), 0.1% sodium azide, pH 7.0, and then poured into the barrel of a filter device. The syringe plunger was inserted into the filter device and pressed down to expel the filtered sample through the end of the syringe into a tube. Using a disposable transfer pipet, 0.5 ml of sample was taken from the tube and transferred to the exposed membrane in the immunoassay device described above.

After the sample drained through the membrane in the device, the antibody GL.5 conjugated to alkaline phosphatase was applied in a volume of 140 µL and incubated for 3 minutes. The antibody conjugate concentration was approximately 10 µg/ml. After the incubation, six drops of wash solution containing 100 mM Tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/l of nitro blue tetrazolium (NBT) were applied from a dropper bottle. After the wash drained into the membrane, another six drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature.

At the end of the incubation time, the presence of any visually detectable purple to black lines was noted. The positive control zone described above developed a clearly visible line that resulted from the binding of the antibody-alkaline phosphatase conjugate to the immobilized complex of antigen and antibody. Control samples containing α-1-giardin spiked from purified preparations of recombinant protein to concentrations of 1.5 ng/ml or greater resulted in a visible line at the zone for the detection of this antigen. The negative control zone for the detection of non-specific binding of reagents developed a visible response for less than 1% of the clinical samples tested. When tested again using ¼ of the initial sample volume, no visible response was observed at the negative control zone for any of the samples.

E. Sensitivity of Assay with Purified Antigen

The purified recombinant antigen was serially diluted in a solution containing 1% bovine serum albumin, 10 mM 3-(N-morpholino)propanesulfonic acid (Fisher Scientific, Pittsburgh, Pa.), 150 mM sodium chloride, and 0.1% sodium azide, pH 7.0, and dilutions were tested in replicates of ten using the same procedure employed with stool samples, a tenfold dilution of a 0.5-ml sample followed by filtration of the diluted sample. The lowest concentration of the antigen that consistently produced a positive visual response at the detection zone on the membrane was determined to be the limit of sensitivity of the assay. For α-1-giardin, this was found to be 1.5 ng/ml.

F. Clinical Sensitivity and Specificity of the Assay

The clinical sensitivity and specificity of the assay was determined by testing 444 samples obtained from a patient population in Mexico and Peru. The results were compared to those obtained with a standard ova and parasite examination and with a commercially available enzyme-labeled microtiter plate immunoassay (Alexon ProSpecT *Giardia* Microplate Assay). Discrepancies between methods were resolved by comparing the three results for a discrepant sample. Since no method exists that can unequivocally identify the presence of the organism in samples, when two of the three methods produced the same result, that result was judged to be the correct result for that sample. Clinical sensitivity, specificity, positive predictive value and negative predictive value were calculated as described in the *Tietz*

Textbook of Clinical Chemistry (second edition, page 496). The results are shown in Table 4-Table 6. The assay for α-1-giardin was shown to be more sensitive than traditional ova and parasite methods for the detection of *Giardia lamblia* in clinical samples. Furthermore, the assay of the present invention was substantially equivalent to a commercially available immunoassay that detects a different antigen.

TABLE 4

| | | O & P Evaluation | | |
|---|---|---|---|---|
| | | + | − | Total |
| Triage ® G. lamblia | + | 135 | 35 | 170 |
| | − | 7 | 267 | 274 |
| | Total | 142 | 302 | 444 |
| Sensitivity | | | 95.1% | |
| Specificity | | | 88.4% | |
| Positive Predictive Value | | | 79.4% | |
| Negative Predictive Value | | | 97.4% | |

TABLE 5

| | | Alexon | | |
|---|---|---|---|---|
| | | + | − | Total |
| Triage ® G. lamblia | + | 163 | 7 | 170 |
| | − | 17 | 257 | 274 |
| | Total | 180 | 264 | 444 |
| Sensitivity | | | 90.6% | |

TABLE 5-continued

| | Alexon | | |
|---|---|---|---|
| | + | − | Total |
| Specificity | | 97.3% | |
| Positive Predictive Value | | 95.9% | |
| Negative Predictive Value | | 93.8% | |

TABLE 6

| | | Resolved | | |
|---|---|---|---|---|
| | | + | − | Total |
| Triage ® G. lamblia | + | 163 | 7 | 170 |
| | − | 3 | 271 | 274 |
| | Total | 166 | 278 | 444 |
| Sensitivity | | | 98.2% | |
| Specificity | | | 97.5% | |
| Positive Predictive Value | | | 95.9% | |
| Negative Predictive Value | | | 98.9% | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of diagnosing infection of a mammal by a *Giardia* species, the method comprising:

contacting a stool sample obtained from the mammal with a capture reagent which binds to an α-1-giardin of *Giardia lamblia*, wherein the capture reagent forms a complex with the α-1-giardin if present in the stool sample; and detecting whether the α-1-giardin is bound to the capture reagent, wherein the presence of the α-1-giardin is indicative of *Giardia* infection of the mammal.

2. The method of claim 1, wherein the capture reagent comprises an antibody which specifically binds to the α-1-giardin.

3. The method of claim 2, wherein the antibody is a recombinant polyclonal antibody.

4. The method of claim 3, wherein the recombinant polyclonal antibody preparation is GL.18.PC produced by a cell line having ATCC accession number 98853.

5. The method of claim 1, wherein the capture reagent is immobilized on a solid support.

6. The method of claim 5, wherein the capture reagent is immobilized on the solid support prior to contacting the capture reagent with the test sample.

7. The method of claim 1, wherein the detection of the α-1-giardin is performed by contacting the α-1-giardin with a detection reagent which binds to the α-1-giardin.

8. The method of claim 7, wherein the detection reagent comprises an antibody which binds to the α-1-giardin.

9. The method of claim 8, wherein the antibody is a monoclonal antibody.

10. The method of claim 9, wherein the monoclonal antibody is GL.5 produced by a cell line having ATCC accession number 98858.

11. The method of claim 7, wherein the detection reagent comprises a detectable label.

12. The method of claim 11, wherein the detectable label is selected from the group consisting of a radioactive label, a fluorophore, a dye, an enzyme, and a chemiluminescent label.

13. The method of claim 12, wherein the enzyme is alkaline phosphatase.

14. The method of claim 2, wherein the antibody is a monoclonal antibody.

15. The method of claim 14, wherein the monoclonal antibody is GL.5 produced by a cell line having ATCC accession number 98858.

16. The method of claim 1, wherein the stool sample is diluted with a sample diluent and filtered prior to the contacting step.

17. The method of claim 16, wherein the sample diluent comprises 1% casein, 100 mM potassium phosphate, 150 mM sodium chloride, 0/1% dimethicone copolyol, 0.1% bovine IgG, 0.1% sodium azide, ph 7.0.

* * * * *

UNITED STATES PATENT AND TRADEMARK OFFICE
CERTIFICATE OF CORRECTION

PATENT NO. : 6,908,739 B2 Page 1 of 1
APPLICATION NO. : 10/155163
DATED : June 21, 2005
INVENTOR(S) : Joseph Buechler et al.

It is certified that error appears in the above-identified patent and that said Letters Patent is hereby corrected as shown below:

In item (75) on the face page of the patent:

Please change Inventor name "Joe Buechler" to -- Joseph Buechler --.

Signed and Sealed this

Second Day of September, 2008

JON W. DUDAS
*Director of the United States Patent and Trademark Office*

SEQUENCE LISTING

<160> NUMBER OF SEQ ID NOS: 10

<210> SEQ ID NO 1
<211> LENGTH: 75
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer A

<400> SEQUENCE: 1
gtgataaact accgcattaa agcttatcga tgataagctg tcaattagtg atggtgatgg      60
tgatgacaat ccctg                                                      75

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer B

<400> SEQUENCE: 2
acccgttttt ttggatggag tgaaacgatg ccgaaggtca ccgacattg                  49

<210> SEQ ID NO 3
<211> LENGTH: 85

```
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer C

<400> SEQUENCE: 3
gtgataaact accgcattaa agcttatcga tgataagctg tcaattagtg atggtgatgg      60
tgatgcttca cgcgccagag ggtgc                                           85

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer D

<400> SEQUENCE: 4
gcgacggtct cgtgccagtc                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer E

<400> SEQUENCE: 5
ctccgcactc gggacggtgc                                                 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer F

<400> SEQUENCE: 6
tcgtcgccct tgtcattgca g                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer G

<400> SEQUENCE: 7
gcaactctct actgtttctc c                                               21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer H

<400> SEQUENCE: 8
gaggatgacg atgagcgc                                                   18

<210> SEQ ID NO 9
```

```
-continued

<211> LENGTH: 20
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer I

<400> SEQUENCE: 9
tcgctgccca accagccatg                                                    20

<210> SEQ ID NO 10
<211> LENGTH: 75
<212> TYPE: DNA
<213> ORGANISM: Artificial Sequence
<220> FEATURE:
<223> OTHER INFORMATION: Description of Artificial Sequence:Giardia
      lamblia alpha-1-giardin PCR and sequencing primer J

<400> SEQUENCE: 10
gtgataaact accgcattaa agcttatcga tgataagctg tcaattagtg atggtgatgg        60
tgatgacaat ccctg                                                         75
```